United States Patent [19]

Mitschke et al.

[11] 4,289,646

[45] Sep. 15, 1981

[54] 1,1-DIFLUORO-2-CHLOROETHYLENE AS AEROSOL PROPELLANT

[75] Inventors: Karl-Heinz Mitschke, Odenthal; Hans Niederprüm, Monheim, both of Fed. Rep. of Germany

[73] Assignee: Bayer Aktiengesellschaft, Leverkusen, Fed. Rep. of Germany

[21] Appl. No.: 83,900

[22] Filed: Oct. 11, 1979

[30] Foreign Application Priority Data

Oct. 27, 1978 [DE] Fed. Rep. of Germany ....... 2846811

[51] Int. Cl.³ .............................................. C09K 3/30
[52] U.S. Cl. .................................... 252/305; 424/45; 424/47; 570/135

[58] Field of Search ................... 252/305; 424/45, 47; 260/653.3, 653.5

[56] References Cited

U.S. PATENT DOCUMENTS 2,709,181  5/1955  Fredrick .......................... 260/653.5
3,607,745  9/1971  DiPietro .............................. 252/305

Primary Examiner—Deborah L. Kyle
Attorney, Agent, or Firm—Sprung, Felfe, Horn, Lynch & Kramer

[57] ABSTRACT 1,1-Difluoro-2-chloroethylene is used as the propellant in an aerosol spray can. It is reasonably stable and non-flammable but will in time degrade in the atmosphere.

4 Claims, No Drawings

1,1-DIFLUORO-2-CHLOROETHYLENE AS AEROSOL PROPELLANT

The present invention relates to a new propellant gas for aerosols which enables the active ingredient/solvent mixture to be very finely atomized.

It is known that the most important propellant gases for aerosols are the perhalogenated fluorochloroalkanes $CCl_3F$ (R 11), $CCl_2F_2$ (R 12) and $CClF_2$—$CClF_2$ (R 114). Recently, however, considerable interest has been shown in the replacement of these conventional propellant gases by propellant gases having different properties, for example higher degradability. These new propellant gases should, of course have properties otherwise equally favorable to those of the conventionally used fluorochloroalkanes. However, the resulting inevitable reduction in chemical stability should not lend to the formation of physiologically harmful products because, of course, the propellant gases are also to be used for the quantitatively important sectors of hairsprays and body sprays.

In addition to the aforementioned fluorochloroalkanes having non-inflammable and, in addition, fire-retarding properties, other propellant gases have already been used in the aerosol field, for example hydrocarbons such as propane, butane, and isobutane, and compressed gases, such as $N_2$, $N_2O$ or $CO_2$ (cf. for example I.I. Sciarra and L. Stoller, The Science and Technology of Aerosol Packaging, John Wiley, New York, 1974, and The Aerosol Handbook, Wayne E. Dorland Co., Caldwell, New Jersey (1972)).

Hydrocarbons have the serious disadvantage, however, of being highly inflammable, and they can form explosive propellant gas/air mixtures. This is not only dangerous to the user of an aerosol, but also complicates packaging, transport and storage. In cases where hydrocarbons are used, strict safety precautions have to be taken, particularly for packaging purposes.

Compressed gases such as, for example, nitrogen or air are unsuitable in practice for producing genuine aerosols. In addition, compressed gases which also show limited solubility in the solvents generally used ($CO_2$ or $N_2O$) do not enable a constant-pressure aerosol to be produced. In other words the spray parameters thereof change continuously with use of the liquid filling. Furthermore, it is necessary in cases where, for example, $CO_2$ or $N_2O$ are used, to employ very large quantities of inflammable solvents, such as acetone or ethanol.

It has also been proposed to use the technical products $CHF_2Cl$ (R 22), a low-temperature refrigerant and a starting material for PTFE, and $CF_2Cl$—$CH_3$ (R 142 b), a starting material for fluorinated plastics and elastomers, or mixtures thereof as propellant gases (M. Bhuta, Aerosol Age, December 1976, page 45). However, R 142 b is inflammable (explosion limit in air 9.0/14.8%), while R 22 can only be used to a limited extent on its own because of its low boiling point ($-40.8°$ C.) and, hence, its high vapor pressure at room temperature.

1,1,1-Trifluoro-2-chloroethane (R 133 a) has also been used as a propellant gas. Thus, R 133 a has been proposed for certain aerosol formulations, its increased solubility in water, in comparison with conventional fluorochlorinated hydrocarbons, having been utilized for example for shaving creams (cf. German Auslegeschrift No. 1,542,076).

Due to its relatively high boiling point (approximately 7° C.), 1,1,1-trifluoro-2-chloroethane has to be used in admixture with so-called "low boilers", such as for example the standard fluorochlorinated hydrocarbon R 12 (U.S. Pat. No. 3,585,921), with hydrocarbons such as, for example, propane and/or butane, or with carbon dioxide and or nitrogen peroxide in order to satisfy the requirements for a genuine aerosol product.

The present invention provides a propellant gas for aerosols which is characterized in that it contains 1,1-difluoro-2-chloroethylene.

The present invention also relates to the use of 1,1-difluoro-2-chloroethylene as a propellant gas.

According to application Ser. No. 83,898 filed Oct. 11, 1979, now abandoned (corresponding to German application No. P 2846 812.4), the disclosure of which is incorporated herein by reference, 1,1-difluoro-2-chloroethylene, a compound known per se, with as yet no appreciable technical significance, may be produced in high yields by dehydrohalogenating 1,1-difluoro-1,2-dichloroethane with aqueous bases under pressure and at elevated temperature in the absence of such auxiliaries as organic solvents and emulsifiers. The process in question is generally carried out by initially introducing one of the reaction components into a pressure vessel provided with the usual attachments, such as for example a stirrer, a pressure cooler, and pressure stabilizing valves, and then adding the other reaction component, preferably the basic reacting substance, dissolved or suspended in water. The 1,1-difluoro-2-chloroethylene formed during the reaction is continuously condensed in traps which are cooled to around $-70°$ C. and, after drying (for example with calcium chloride), it is distilled. Distillation may be carried out under pressure or at normal pressure. Any starting material remaining in the sump may optionally be re-used for the reaction. 1,1-Difluoro-1,2-dichloroethane may itself be obtained by catalytically fluorinating trichloroethylene in the liquid phase.

By virtue of its chemical structure, 1,1-difluoro-2-chloroethylene may be attacked, i.e. is degradable, and may therefore be regarded as a substitute for the conventional fluorochlorinated hydrocarbons in aerosol formulations. On spraying into a Bunsen burner flame, no stationary combustion is observed. It is only in a closed apparatus, and by applying very intense ignition energy (approximately 20 joules) that lower and upper ignition limits of 10.1% by volume and 41.3% by volume in air are observed. The compound has good solubility properties and does not adversely affect the perfuming of aerosols. In addition, the favorable boiling point of this compound (approximately $-18°$ C.) gives a pressure at 20° C. of approximately 3.5 bars which substantially corresponds to that of the 50/50 mixture of the conventional fluorochlorinated hydrocarbons R11 and R12, so that no additional "pressure intensifiers" or "pressure reducers" are required for obtaining good spray properties.

Suitable solvents for the active substances are, for example, ethanol, ethyl acetate, isopropanol, acetone, methyl chloroform, methylene chloride or mixtures of these solvents. It is also possible to use fluorine containing solvents such as, for example, $CF_2Cl$—$CFCl_2$ and $CF_2Cl$—$CH_2Cl$.

The propellant gas is best added in a quantity commensurate with the purpose for which the aerosol is to be used, as is known per se. In general, the propellant gas content amounts to between about 8 and 92% by weight and, in some cases, to as much as about 96% by weight (based on the total content of the aerosol contents), depending on whether a foam (low propellant gas content), a surface spray (medium propellant gas content) or a genuine aerosol (high propellant gas content) is to be dispensed.

The propellant gas according to the present invention may be used for all kinds of spray systems such as, for example, hair sprays, body sprays, room and insecticide sprays, polishes, lacquers, suntan sprays, shaving foams, shampoos, cleaning foams, car-care sprays, condiment sprays or silicone sprays.

The present invention is further illustrated by the following non-limiting examples.

EXAMPLE 1

Aerosol Body Spray 0.5% by weight of 2,4,4'-trichloro-2'-hydroxy diphenyl ether, 1.0% by weight of a triglyceride mixture of saturated vegetable fatty acids having medium chain length and 1.0% by weight of a standard commercial perfume oil were dissolved in 32.95% by weight of ethanol. This filling was introduced into a 6 oz aerosol can and made up with 65.0% by weight of the propellant 1,1-difluoro-2-chloroethylene. The can was clinched with a standard commercial valve (for example Co-10/goldl. 0.3). The spray head used was also of a standard commercial type.

Subsequent pressure measurement indicated a pressure of 3.3 bars at 20° C. As in the following examples, the spray characteristics corresponded to that of an aerosol can filled with conventional propellants.

EXAMPLE 2

Aerosol Hairspray

A mixture of 5.0% by weight of polyvinyl pyrrolidone/vinylacetate (30:70), 14.8% by weight of methylene chloride, 20.0% by weight of isopropanol and 0.2% by weight of a standard commercial perfume oil was introduced into a 6 oz. aerosol can with 60% by weight of the propellant 1,1-difluoro-2-chloroethylene, ater which the procedure of Example 1 was followed. Pressure measurement at 20° C. indicated a pressure of 3.0 bars. The filling had the same properties as a standard commercial product.

EXAMPLE 3

Aerosol Room Spray 19.0% by weight of ethanol, 1.0% by weight of a standard commercial perfume oil and 80.0% by weight of the propellant 1,1-difluoro-2-chloroethylene were introduced into a 6 oz. aerosol can, after which the procedure as Example 1 was followed. Subsequent pressure measurement at 20° C. indicated a pressure of 3.5 bars.

EXAMPLE 4

Aerosol Shaving Foam 6.8% by weight of stearic acid, 3.7% by weight of triethanolamine, 0.5% by weight of polyethylene glycol (molecular weight 1550), 0.5% by weight of alkanolamide, 0.25% by weight of polyethylene glycol (molecular weight 6000), 2.0% by weight of glycerol, 1.0% by weight of propylene glycol stearate and 84.25% by weight of distilled water were heated together to approximately 70° C. and thoroughly stirred. After cooling to approximately 40° C., 1.0% by weight of a standard commercial perfume was added to the mixture with stirring.

90.0% by weight of this filling was introduced with 10.0% by weight of the propellant 1,1-difluoro-2-chloroethylene into a 6 oz. aerosol can which was then provided with a standard commercial valve and foam head. After the can had been shaken, an extremely fine foam was obtained.

EXAMPLE 5

Aerosol Insecticide Spray

20% by weight of filling (standard commercial insecticide based on DDVP and synthetic pyrethrum) and 80% by weight of the propellant 1,1-difluoro-2-chloroethylene were introduced into a 6 oz. aerosol can which was then sealed as described in Example 1. The filling had the same properties as a standard commercial product.

EXAMPLE 6

Aerosol Silicone Spray

4% by weight of a polydimethylsiloxane oil having a viscosity of 300 cSt was introduced with 96% by weight of the propellant 1,1-difluoro-2-chloroethylene into a 6 oz. aerosol can which was then sealed following the procedure of Example 1. The filling had the same properties as a standard commercial product.

It will be appreciated that the instant specification and examples are set forth by way of illustration and not limitation and that various modifications and changes may be made without departing from the spirit and scope of the present invention.

We claim:

1. A container for dispersing a spray comprising a container, a valve sealing the container, a conventional filler within said container to be dispersed as a spray and a pressurized propellant gas comprising 1,1-difluoro-2-chloroethylene.

2. A container according to claim 1, wherein the propellant gas comprises from about 8 to 96% by weight of the total contents of the container.

3. A container according to claim 1, wherein the propellant gas comprises from about 8 to 92% by weight of the total contents of the container and the pressure within the container is from about 3 to 3.5 bars at 20° C.

4. In the dispersing of a material as an aerosol by opening a valve on a pressurized container containing a filler to be dispersed and a propellant, the improvement which comprises employing 1,1-difluoro-2-chloroethylene as the propellant.

* * * * *